United States Patent [19]

Woods

[11] Patent Number: 4,650,461
[45] Date of Patent: Mar. 17, 1987

[54] EXTRACAPASULAR CORTEX IRRIGATION AND EXTRACTION

[76] Inventor: Randall L. Woods, 1704 Nicklaus, Clinton, Mo. 64735

[21] Appl. No.: 830,238

[22] Filed: Feb. 18, 1986

Related U.S. Application Data

[63] Continuation-in-part of Ser. No. 743,267, Jun. 10, 1985, abandoned, which is a continuation of Ser. No. 587,130, Mar. 7, 1984, abandoned, which is a continuation-in-part of Ser. No. 501,646, Jun. 6, 1983, abandoned.

[51] Int. Cl.⁴ .............................................. A61M 1/00
[52] U.S. Cl. ...................................... 604/28; 604/30; 604/35; 604/37
[58] Field of Search .................. 604/30, 19, 22, 27, 604/28, 35, 36, 37, 43, 34, 118

[56] References Cited

U.S. PATENT DOCUMENTS

| | | |
|---|---|---|
| 386,603 | 7/1898 | Parsons . |
| 1,493,592 | 5/1924 | Beck . |
| 2,874,696 | 2/1959 | Bried . |
| 3,780,736 | 12/1973 | Chen . |
| 3,818,913 | 6/1974 | Wallach . |
| 3,902,495 | 9/1975 | Weiss et al. ............................ 604/22 |
| 3,906,954 | 9/1975 | Baehr et al. . |
| 3,930,505 | 1/1976 | Wallach . |
| 3,994,297 | 11/1965 | Kopf . |
| 3,996,935 | 12/1976 | Banko ............................... 604/28 X |
| 4,014,333 | 3/1977 | McIntyre . |
| 4,029,095 | 6/1977 | Pena . |
| 4,084,612 | 4/1978 | Baehr ............................... 604/118 X |
| 4,184,510 | 1/1980 | Murry et al. ...................... 604/22 X |
| 4,274,411 | 6/1981 | Dotson, Jr. ............................. 604/30 |
| 4,300,571 | 11/1981 | Waldbillig . |
| 4,324,243 | 4/1982 | Helfgott et al. .................. 604/22 X |
| 4,428,748 | 1/1984 | Peyman et al. ...................... 604/22 |
| 4,465,470 | 4/1984 | Kelman ................................. 604/27 |
| 4,496,342 | 1/1985 | Banko ................................... 604/27 |

FOREIGN PATENT DOCUMENTS

673280 7/1979 U.S.S.R. ................................ 604/30

OTHER PUBLICATIONS

Staar Surgical Company BecStop TM Sterilizing Filter, Brochure, Staar Surgical Co. Monrovia CA. No date p. 4.
"Elimiation of Contaminaiton From Alphthalmic Surgery, Etc." by Norman Jaffe, M.D. American Academy of Opthalmology, etc., vol. 74(2), 1970, pp. 406–416.
"Effects of Intraocular Irrigating Solutions, etc." by Glaser et al, American Journal of Ophthalmology 99:321–328, Mar. 1985.
"Prevention of Endophthalmitis etc." by James Gills, M.D. AM Intra-Ocular Implant Soc. Journal-vol. 11, Mar. 1982, pp. 185–186.
"More on Contaminations, etc." and Contamination of Irrigating Solution etc. Letters to the Editor, *Ophthalmic Surgery*, Jun. 1984, vol. 15, No. 6, pp. 534–535.

*Primary Examiner*—William H. Grieb
*Attorney, Agent, or Firm*—Schmidt, Johnson, Hovey & Williams

[57] ABSTRACT

In the surgical art of extracapsular cataract extraction, the lens capsule of the eye is irrigated and aspirated for cortex removal through use of a simple, inexpensive system of circulation of an irrigating solution, accompanied by automatic filtering of the aspirated material out of the solution such that the filtered liquid may be reintroduced. Means are included to produce unidirectional flow, and a manually operable bypass feature provides for safety and operator control of the entire procedure to assure accuracy, efficiency, exactitude and the best possible end results. The system is kept filled with the liquid solution in substantial absence of air therewithin.

22 Claims, 10 Drawing Figures

EXTRACAPASULAR CORTEX IRRIGATION AND EXTRACTION

This is a continuation-in-part of application Ser. No. 743,267, filed June 10, 1985, which is a continuation of application Ser. No. 587,130, filed Mar. 7, 1984, which is a continuation-in-part of application Ser. No. 501,646, filed June 6, 1983, all now abandoned.

The instant invention relates to extracapsular cataract surgery during which the nucleus and the cortex of the lens are removed while leaving the posterior capsule in place. In certain patients undergoing extracapsular extraction there subsequently involves the need to correct secondary clouding by removal of further cortex formation on the anterior surface of the posterior capsule.

While equipment and techniques are available for such cortex extraction, ophthalmologists must be specially trained whereas intracapsular surgery is much less complicated. Moreover, costly and sophisticated irrigation and aspiration systems for washing out the peripheral portions of the cataract limit the extent to which extracapsular extraction is practiced among eye surgeons generally.

Therefore, there is a need for techniques and expensive surgical tools in order to permit more widespread extracapsular procedures and avoid the need for the less desirable intracapsular practices now prevailing. Meeting such need and solving the current problems constitute the subject matter of my present invention.

I provide a closed, circulation method of extracting the cortex both during initial cataract surgery, and subsequently from the posterior capsule, by injecting an irrigating fluid under pressure and aspirating the lens chamber to withdraw liquid and the cortex material entrained therein. The flow to and from the chamber is unidirectional and filtering of the cortex material out of the liquid may take place during irrigation and aspiration. The filtered liquid may then be reintroduced for further irrigation.

A tubular instrument is employed, having both outlet and inlet means for the liquid. It is coupled with a liquid circulating tube and the filter in the tube is located downtream of the inlets. A suitable instrumentality is employed between the filter and the outlet of the instrument for effecting the circulating function of the equipment.

In addition to the use of properly located valves in the tube, I provide a fluid bypass which may be used as needed whenever, for whatever reason, free liquid flow is to be impeded, flow is to be discontinued during cortex extraction or suction is to be released at the inlet.

IN THE DRAWINGS

Figure 1:
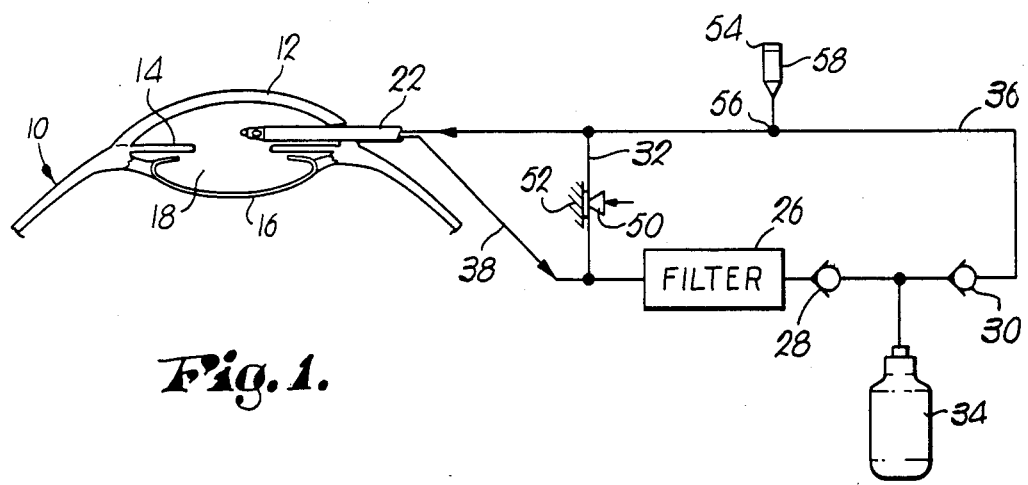
FIG. 1 is an essentially schematic view showing the novel method of one form of my present invention and the equipment employed for such purpose.

Referring first to FIGS. 1-4 of the drawings, certain parts of the human eye 10 following extracapsular cataract surgery as shown in FIG. 1 include the cornea 12, the iris 14 and the posterior capsule 16, it being understood that the entire chamber 18 following such type of surgery is normally filled with aqueous humor.

The equipment employed in accordance with the invention includes a tubular handpiece 20, carrying an instrument 22 insertable in the manner shown by FIG. 1. Additionally, there is provided a flexible tube 24 (extending through the handpiece 20 and communicating with the needle-like instrument 22), a filter 26 and a pair of one way valves 28 and 30 in the tube 24 and, if needed, a flexible by-pass line 32. A liquid pump in the nature of a hollow, flexible syringe 34, capable of manual squeezing communicates with the tube 24 between the valves 28 and 30.

While a variety of known filters can be used in the context of the invention, particularly good results have been obtained with a commercially available filter system designated "BacStop" and sold by Staar Surgical Co. of Monrovia, Calif. The "BacStop" system includes a continuous, hydrophilic microporous film filter media formed of nylon 66 material having a pore size of 0.2 mincrons and rated at a particle removal capability of 0.2 microns, and pyrogen retention of more than twenty-four hours. The media provides the added capability of reducing endotoxins, released from bacteria retained by the filter during infusion, to below detectable levels. The filter is also capable of removing negatively-charged contaminants smaller than 0.2 microns. The total surface area of the filter membrane is relatively large, approximately 224 square centimeters when unfolded. The media admits of relatively high flow rates, e.g., at 25" bottle height, irrigation flow through a properly primed filter is greater than 100 ml. per minute. The product is described in a bulletin entitled "BacStop ™ Sterilizing Filter: In-Line Filtration of Ophthalmic Irrigating Solutions", such bulletin being incorporated by reference herein.

Another type of filter usable in the invention is commercialized by Storz, 3365 Tree Stree, Industrial Blvd., St. Louis, Mo. The specific product is listed in the Storz catalog as paper filter No. E-4429-45. It is believed that the Storz material is formed of nylon.

While the above-described commercial filters have a high degree of utility, the relatively large particles requiring filtering in the present invention can be successfully removed by using common, ordinary white sand as the filter media. Such sand is availabe from a variety of sources.

The tube 24 has a liquid discharge line 36 integrally and continuously connected with a liquid return line 38, and the filter 26 is disposed in the line 38 downstream of the instrument 22. As noted, the valve 28 is in the line 38 downstream of the filter 26 whereas the valve 30 is in the line 36. In effect then, the syringe 34 registers with the tube 24 between the lines 36 and 38. The by-pass line 32 interconnects the lines 36 and 38 upstream of the valve 30 and between the instrument 22 and the filter 26.

Portions of the lines 36 and 38 extend into and along the handpiece 20 in side-by-side relationship and communicate with the instrument 22 via connectors 40 within nozzle 42 of the handpiece 20. The terminal end of the instrument 22 has an axial inlet 44 in communication with the line 36 and a pair of diametrically opposed outlets 46 communicating with the line 38.

Figure 2:
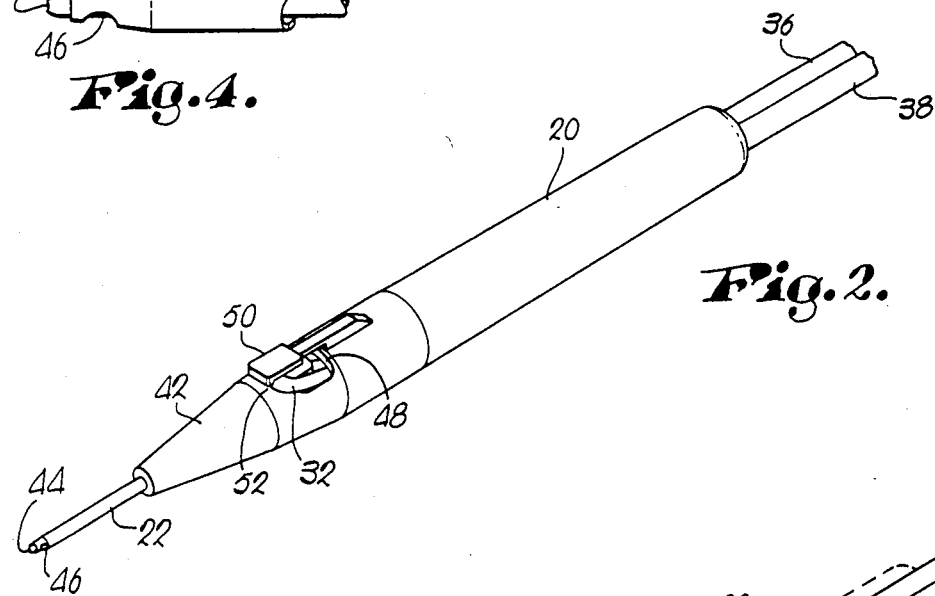
FIG. 2 is an enlarged, fragmentary perspective view of one type of handpiece with an associated fluid injecting and aspirating instrument as well as a bypass control which may be employed in any one or all forms of the instant invention.

Any suitable means may be provided to permit manual squeezing of the line 32 to preclude flow of liquid therethrough from the line 36 to the line 38. As shown in FIG. 2, the handpiece 20 has an opening 48 adjacent the bight of the loop (see FIG. 3) which forms the line 32, and a depressible fingerpiece 50 is provided on the handpiece 20 for inward actuation into the opening 38 in closing relation to the line 32 at its bight against an anvil 52 (FIG. 1) within the handpiece 20.

OPERATION

It is contemplated that a balanced salt solution, capable to the nature of the aqueous humor in chamber 18, will be used to initially fill the tube 24 by inserting the instrument 22 into the liquid of a supply container and effecting withdrawal by use of the syringe 34. This step is continued as long as is needed in order to exhaust all air and assure complete filling of the tube 24 and all other parts of the tool with the liquid. A small incision is made in the eye 10 and the instrument 22 inserted into the chamber 18 as shown in FIG. 1. There should be a minimum of leakage of liquid out of the eye 10 through the incision around the instrument 22 or entrance of air into the eye 10. By grasping the handpiece 20 in one hand and squeezing the syringe 34 in the other hand, the eye surgeon forces the fluid to flow past the valve 30, through the line 36 and into the chamber 18 as the line 32 is held closed by depressing fingerpiece 50. As the liquid exits the outlets 46 under pressure, the handpiece 20 is manipulated such as to direct the stream against the cortex buildup of the inner anterior surface of the capsule 16 within the chamber 18.

The irrigating function of the equipment fragments the cortex such that is can be aspirated from the chamber 18. Initially the aqueous humor is replaced by a filling of the saline solution, but for the most part, the solution and the loosened cortex contained therein pass from the chamber 18 into the line 38 via the inlet 44 of the instrument 22.

Upon release of the syringe 34, the suction created by the syringe 34 will withdraw materials from the eye 10 for removal by the filter 26, all without any counterflow by virtue of the action of the valves 28 and 30. Hence, the filtered solution flows from the filter 26 to the line 36 and is reintroduced into the chamber 18 when the syringe 34 is squeezed once again, all without substantial interruption. As the action on the syringe 34 is continued, irrigation, fragmentation, aspiration and filtering take place successively in the closed, recirculation system illustrated and above described.

In using the improved equipment to carry out my novel method, care can easily be exercised to maintain sufficient liquid pressure in the cavity 18 to avoid collapse of the capsule 16. Also, surgeons skilled in this art will have little difficulty manipulating the tip of the instrument 22 such as to closely scan the cortex build-up without causing damage to the anterior surface, or for that matter, the cornea 12, the iris 14 and other parts of the eye 10.

In the event tissues becomes lodged in the inlet 44, the surgeon can quickly and easily release the fingerpiece 50 causing flow from the line 36 to the line 38 through the line 32.

The finger piece 50 may also be released in the event of any occurence which might prevent or impede free, continuous flow into and out of the chamber 18. For example, if the tip of the instrument 22 is inadvertently brought so close to any portion of the interior surface of the chamber 18 as to shut off the outlets 46 and/or the inlet 44, bypassing of the liquid flow can be accomplished instantaneously. Further, if the cortex materials or unwanted tissue, e.g., from the posterior surface or the iris 14, should block the inlet 44 or cause blockage anywhere along the tube 24, opening of the line 32 under the immediate control of the surgeon, will preclude flow into and out of the chamber 18.

The safety features above enumerated are even more important if means other than the hand held syringe 34 is used to cause recirculation of the solution. A roller pump or many other types of mechanical or electrical devices may be substituted for the syringe 34. In such case, if the control thereof is not easily and quickly responsive to action by the surgeon, no dangers are presented because of the incorporation of the line 32 and fingerpiece 50.

Manifestly, all of the above is equally applicable to cortex extraction during extracapsular cataract surgery, the instrument 22 then being inserted through the incision normally cut into the eye 10 for such purposes. Here again, care should be taken to close the incision sufficiently around the instrument 22 so as to prevent loss of liquid from the eye 10 and preclude entrance of air thereinto.

From the foregoing, it can now be appreciated that the costs to the cataract surgeon in equipment are substantially reduced; the handpiece 20 and all associated parts can even be disposable, limited to a single use, thereby maintaining sterile conditions. Expenses are also reduced by the fact that a minimum amount of irrigating liquid is needed for each complete irrigation and aspiration procedure. Moreover, my system opens up the art of extracapsular cataract extraction for practice by substantially the entire ophthalmic profession.

While the tool is being used there will be a loss of the liquid through leakage from the eye 10 or absorption by the tissues within the eye 10. In that event, in order to refill the tool with the liquid to full capacity it is but necessary to pierce a membrane 54 at T-connection 56 in line 26 with a needle exhausting from a liquid supply container to a receiver 58. The membrane 54 is self-closing upon removal of the needle as is well known.

From the foregoing it is important to note that air in the system which might damage the cornea 12 has been eliminated. Moreover, substantially absent of air, the tool is fully and immediately responsive to the acts of the user in effecting the circulation and in causing liquid bypass, when desired, by actuation of the fingerpiece 50.

Figure 4:
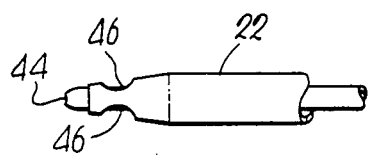
FIG. 4 is an enlarged side elevational view of the aforementioned instrument shown in FIGS. 1-3.
Figure 3:
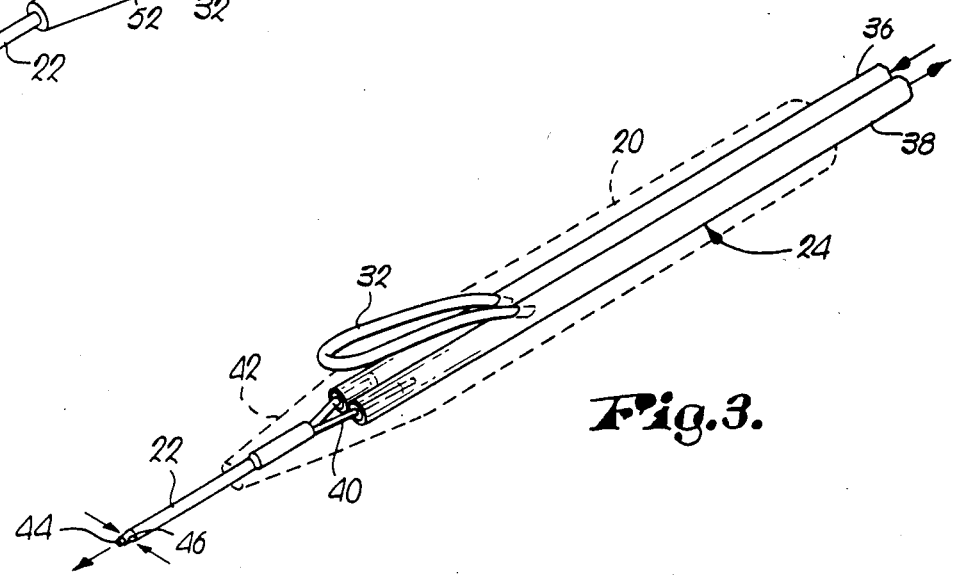
FIG. 3 is a fragmentary, perspective view similar to FIG. 2 with the handpiece in phantom to depict the part therein contained.
Figure 5:
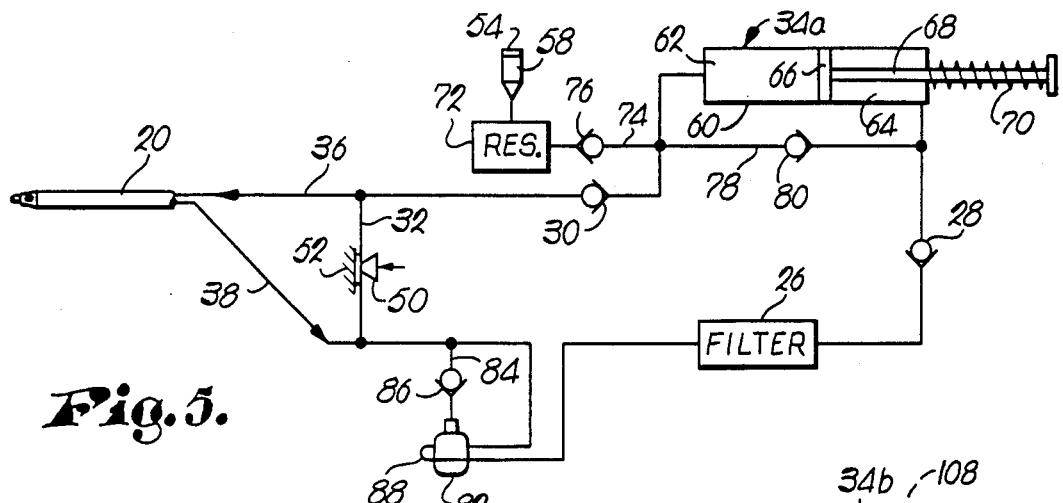
FIGS. 5-7 are views similar to FIG. 1 showing three additional embodiments of the present invention.
Figure 6:
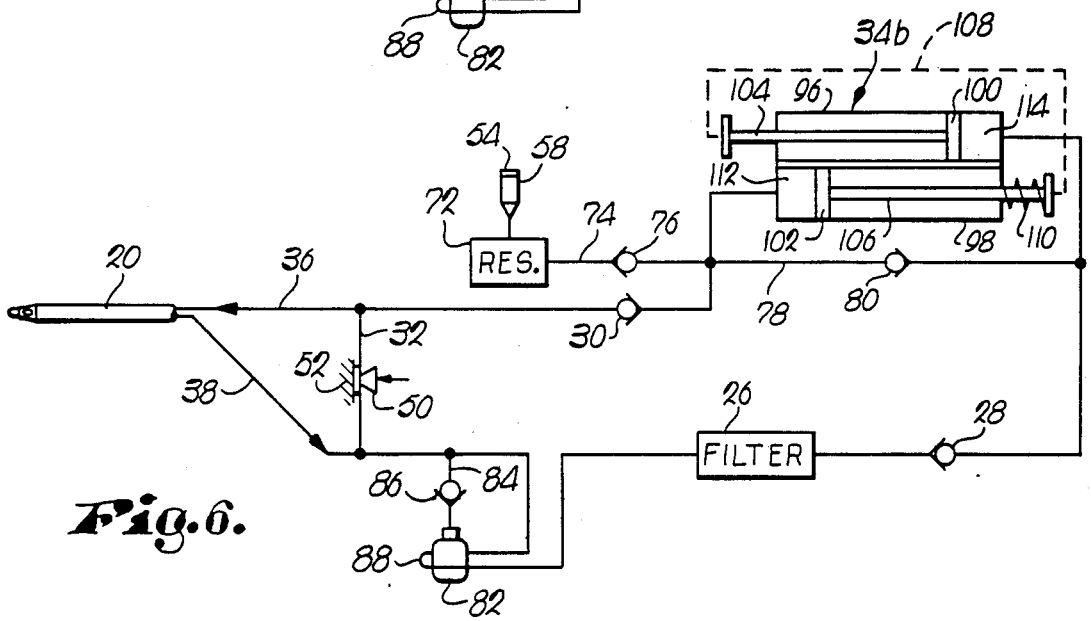
Figure 7:
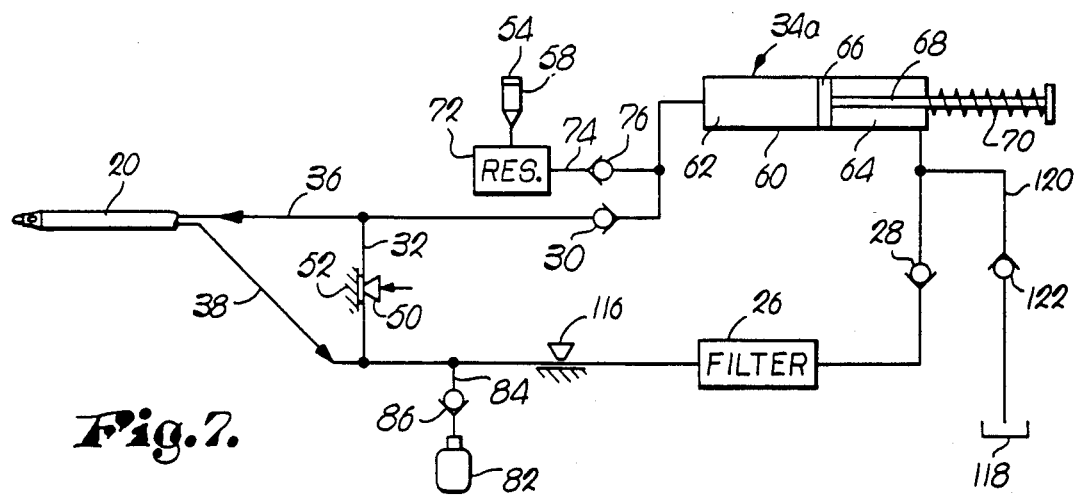

All of the embodiments of FIGS. 5–7, 9 and 10 may employ the same handpiece 20 shown in FIGS. 2–4, inserted into the chamber 18 as illustrated in FIG. 1 and with the exception of the forms shown in FIGS. 5–7 in which the bypass line 32 is not needed and all employ the same bypass line 32 with the fingerpiece 50 as shown in FIGS. 1, 2 and above explained. Thus, each such embodiment also has the same discharge line 36 and return line 38, and the filter 26 is shown in each instance, but the syringe 34 is not used. Moreover, the same valves 28 and 30 are provided in each of the modifications and, in each instance, the receiver 58 and its membrane 54 are included.

However, as shown by FIG. 5, in lieu of the syringe 34, there is provided a liquid pump 34a in the nature of a spring-loaded piston and cylinder assembly. It includes a cylinder 60 separated into two compartments 62 and 64 by a reciprocable piston 66, the compartment 62 being connected with the line 36 and the compartment 64 being connected to the line 38. A rod 68 connected to the piston 66 in the compartment 64 reduces the capacity of the latter as compared with the volume of liquid cability of the compartment 62. A spring 70 coiled about the rod 68 exteriorly of the cylinder 60 yieldably biases the piston 66 to its retracted position shown in FIG. 5.

Liquid from the receiver 58 flows to a reservoir 72 and such liquid may pass to the line 36 via a first branch 74 provided with a one-way valve 76 for precluding reverse flow to the reservoir 72. A second branch 78 connected with the branch 74 and with both of the line 36 and 38 has a one-way valve 80 for precluding liquid flow to the line 38.

Squeeze bottle 82 has a connection 84 with the line 38 between the bypass line 32 and the filter 26, there being a one-way valve 86 in the connection 84 for precluding flow of liquid from the eye 10 to the bottle 82. A portion 88 of the line 38 is in looped relation to the bottle 82 such that, as the bottle 82 and the loop 88 are hand grasped, liquid is forced from the bottle 82 into the connection 84 and into the line 38 toward the eye 10 and the line 38 is closed by pinching of the loop 88 to preclude flow of liquid from the connection 84 toward the filter 26.

Figure 8:
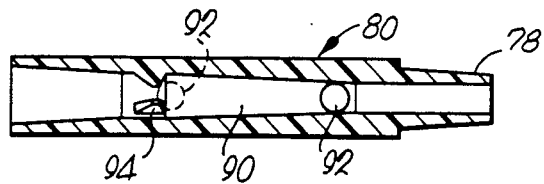
FIG. 8 is a gross sectional view of one type of check valve employed in the modifications of FIGS. 5-7.

The valve 80 is special in nature as shown in FIG. 8 such that, as distinguished from the conventional ball check, the ball does not seat immediately when the liquid flow causes the ball to move toward its seat. Instead, the valve 80 has a tapered passage 90 such that ball 92 therein seats at the smallest end of the passage 90 as shown in FIG. 8 when the flow in branch 78 is toward the valve 28. Conversely, when the liquid flow along the branch 78 is in the opposite direction, the ball 92 moves into engagement with stops 94 in the passage 90 which do not restrict liquid flow. Accordingly, when the ball 92 is in engagement with the stops 94 as shown by dotted lines in FIG. 8, and the direction of flow is such as to move the ball 92 away from the stops 94, the flow continues for a short period until the ball 92 reaches its seated position at the smallest end of the passage 90. The valve 28 is also of the type shown in FIG. 8.

The basic operation of the embodiment of FIG. 5 is essentially the same as that of the form of my invention shown in FIG. 1. The rod 68 is depressed against the action of the spring 70 as the line 32 is held closed by depressing the fingerpiece 50. Liquid is forced from the compartment 62 into the line 36 by the piston 66 and thence to the eye 10 past the valve 30, but is blocked by the valve 76.

At the same time, the compartment 64 is replenished with filtered liquid from the line 38 by the drawing action of the piston 66, causing simultaneous aspiration as the liquid flows through the loop 88 and the filter 26 past the valve 28. During the depression of the rod 68, the pressurized liquid in the line 36 will close the valve 80 after a certain amount of liquid flows to the line 38 during the delayed movement of the ball 92 to its seated position.

In the event it becomes necessary or desirable to back flush the eye 10 to loosen the materials to be removed or unblock the inlet 44, the bottle 82 is squeezed to force liquid through the connection 84 to the line 38 while, at the same time, pinching the loop 88 closed to prevent flow toward the filter 26.

The only difference between the embodiment of FIGS. 5 and 6 is that in the latter a different type of liquid pump 34b is employed. As a composite unit, the pump 34b includes a pair of cylinders 96 and 98 having pistons 100 and 102 respectively provided with corresponding rods 104 and 106. The rods 104 and 106 have a coupling 108 for simultaneous actuation, and a spring 110 is coiled around the rod 106 exteriorly of the cylinder 98. The line 36 connects with one end of the cylinder 98 and line 38 is connected with one end of the cylinder 96.

The embodiment shown in FIG. 7 is similar to that illustrated in FIG. 5 except for elimination of the branch 78 and the valve 80, and the substitution of a separate squeeze closure 116 in the line 38 between the filter 26 and the connection 84 in lieu of the loop 88. Also, a receptacle 118 is provided in FIG. 7 adapted to receive waste from a branch 120 coupled with the line 38 between the valve 28 and the pump 34a. A check valve 122 in the branch 120 permits flow only to the receptacle 118. Liquid drawn from the chamber 64 during return of the rod 68 by the action of the spring 70 will be forced by the piston 66 through the branch 120 and past the valve 122 for flow to the receptacle 118. Simultaneously, liquid will be drawn by the piston 66 into the compartment 62 from the reservoir 72.

Figure 9:
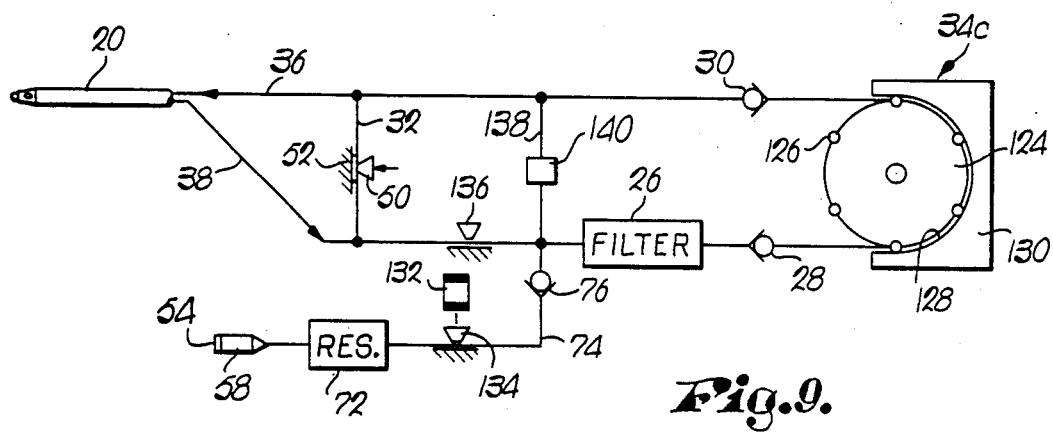
FIGS. 9 and 10 are views similar to FIGS. 1 and 5-7 showing the additional modifications of my instant invention.

In the embodiment of FIG. 9, there is provided a roller type pump 34c in lieu of the syringe 34 shown in FIG. 1. The lines 36 and 38 are directly interconnected around a rotor 124 having transverse rollers 126 spaced around its circumference and adapted to squeeze the flexible lines 36, 38 against an arcuate surface 128 of a rigid member 130 such that, during rotation of the rotor 124, liquid is continuously directed to and away from the eye 10.

Additionally, instead of communicating with line 36 at connection 56 in FIG. 1, the receiver 58 registers with reservoir 72 (as in FIGS. 5–7) and the latter has its branch 74 (with valve 76 therein) connected with line 38 between instrument 22 and filter 26. A solenoid 132 normally holds a squeeze type closure 134 in a position precluding flow of liquid from the reservoir 72. A normally open, manually operable squeeze type closure 136 is provided in the line 38 between the instrument 22 and the connection of the branch 74 with the line 38. The branch 74 continues from the line 38 in an extension 138 which joins with the line 36 between the valve 30 and the bypass line 32. A pressure relief valve 140 is interposed in the extension 138, preset to exhaust liquid from the line 36 to the line 38 when the liquid pressure in the line 36 exceeds a predetermined limit above the pressure in the line 38.

Once again we have simultaneous irrigation and aspiration during rotation of the rotor 124 with replenishment of liquid at will upon energization of the solenoid 132 while the line 38 is held closed by manual operation of the closure 136.

Figure 10:
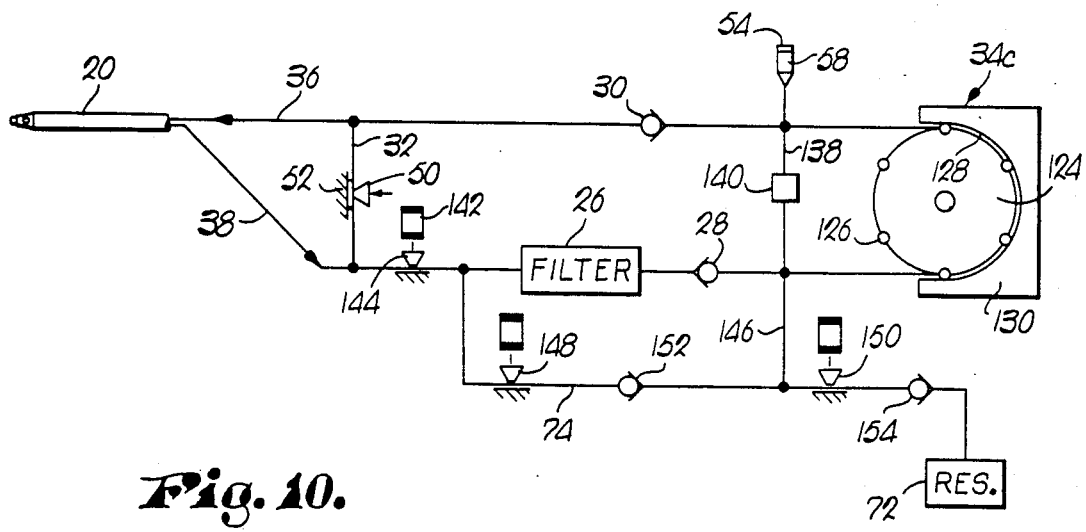

In FIG. 10, a reversible pump 34c is shown in connection with the receiver 58 and the membrane 54 associated with the line 36 as in FIG. 1, and with a solenoid 142 having its normally open closure 144 associated with line 38 in lieu of the closure 136 shown in FIG. 9.

The reservoir 72 has its branch 74 connected with the line 38 the same as in FIG. 9 between the filter 26 and the closure 144, and the extension 138 (with its valve 140) bridges the lines 36 and 38 as in FIG. 9, but downstream of the valve 28. The extension 138 continues from the line 38 in a line 146 which communicates with the branch 74. A first solenoid controlled, normally open squeeze closure 148 and a second solenoid controlled, normally closed squeeze closure 150 for the branch 74 have the line 146 interposed therebetween. A first check valve 152 is provided in the branch 74 between the closure 148 and the line 146 and a second check valve 154 is provided in the branch 74 between the line 146 and the reservoir 72.

The pump 34c may be reversed to backflush the inlet 44 of unwanted material. During such operation, the filter 26 is bypassed, the flow being from the receiver 58 through the lines 36 and 146, past the valve 152, through the branch 74 and the line 38, to the handpiece and thence to the eye 10.

I claim:

1. In a closed, recirculation method of extracting lens material from within the lens capsule of the eye, said method including the steps of:
    injecting a substantially airless lens irrigating liquid under pressure into the capsule;
    aspirating the capsule to withdraw therefrom said liquid and the materials contained therein;
    filtering the material out of the liquid as the capsule is being aspirated; and
    reintroducing the filtered liquid into the capsule.

2. The invention of claim 1; and controlling the liquid for unidirectional flow to and from the capsule.

3. The invention of claim 1; and checking the flow of filtered fluid against counterflow to the capsule.

4. The invention of claim 1 wherein said material is cortex.

5. The invention of claim 1 wherein the anterior surface of the posterior capsule is irrigated.

6. The invention of claim 1 wherein the liquid is a saline solution approximating the composition of the aqueous humor of the eye.

7. The invention of claim 5 wherein the liquid is hand pumped for maximizing direct control of the pressure of the liquid in the capsule to thereby avoid rupturing said posterior capsule.

8. The invention of claim 1 wherein the irrigation and aspiration steps are preceded by removal of the nucleus of the lens during cataract surgery.

9. The invention of claim 1 wherein the irrigation and aspiration steps are carried out to extract cortex formation on the anterior surface of the posterior capsule subsequent to cataract extraction for restoring clarity of the posterior capsule.

10. In a closed, recirculation method of extracting lens material from within the lens capsule of the eye, said method including the steps of:
    injecting a lens irrigation liquid under pressure into the capsule;
    aspirating the capsule to withdraw therefrom said liquid and the material contained therein;
    filtering the material out of the liquid as the capsule is being aspirated;
    bypassing the liquid whenever there is an impediment to free flow of the liuid; and
    reintroducing the filtered liquid into the capsule.

11. A combination irrigating and aspirating hand tool for extracting lens material from within the lens capsule of the eye, said tool including:
    a tubular instrument insertable into said capsule;
    said instrument having a liquid outlet and a liquid inlet;
    a liquid recirculating tube coupled with said instrument,
    said tube being adapted to contain a filling of a substantially airless lens irrigating liquid,
    the tube having a first end communicating with said outlet, a second end communicating with said inlet, and being otherwise closed;
    means for circulating the liquid along the tube into the capsule through said outlet, and for aspirating of the capsule to withdraw from the latter through said inlet the liquid and lens material dislodged by the liquid and entrained in the latter; and
    means in said tube downstream of said outlet for removing said material from the liquid prior to simultaneous reintroduction by said circulating means of the filtered liquid into the capsule.

12. The invention of claim 11 wherein the circulating means is adapted for continuous operation, and wherein irrigation, aspiration, removal of material from the liquid and reintroduction of the liquid are effected continuously during continuous operation of the circulating means.

13. The invention of claim 11, said circulating means being disposed downstream of the material removing means.

14. The invention of claim 11; and means for limiting the liquid to unidirectional flow along the tube.

15. The invention of claim 11; and an instrument-supporting handpiece.

16. The invention of claim 1; and means for refilling said tube with additional liquid in the event of liquid loss during use of the tool.

17. A combination irrigating and aspirating hand tool for extracting lens material from within the lens capsule of the eye, said tool including:
    a tubular instrument insertable into said capsule;
    said instrument having a liquid oulet and a liquid inlet;
    a liquid recirculating tube coupled with said instrument,
    said tube being adapted to contain a filling of a lens irrigating liquid,
    the tube having a first end communicating with said outlet, a second end communicating with said inlet, and being otherwise closed;
    means for circulating the liquid along the tube into the capsule through said outlet, and for simultaneous aspiration of the capsule to withdraw from the latter through said inlet the liquid and lens material dislodged by the liquid and entrained in the latter;
    means for bypassing the liquid in the event of existence of conditions within the capsule tending to impede free flow of the liquid in the tube during operation of said circulating means; and
    means in said tube downstream of said outlet for simultaneously removing said material from the liquid prior to simultaneous reintroduction by said circulating means of the filtered liquid into the capsule.

18. The invention of claim 5 wherein the liquid is pumped continuously into the capsule and withdrawn continuously from the eye.

19. The invention of claim 11 wherein said circulating means comprises a hand operated syringe.

20. The invention of claim 12 wherein said circulating means comprises a manually activated piston and cylinder assembly.

21. The invention of claim 12 wherein said circulating means comprises a pair of piston and cylinder assemblies, one for injecting the liquid, and other for withdrawing the liquid, said assemblies being adapted for simultaneous operation.

22. The invention of claim 12 wherein said tube is flexible and wherein said circulating means comprises a pump having a member adapted for continuous rotation and provided with elements successively squeezing the tube to inject the liquid and releasing the tube to withdraw the liquid.

* * * * *